(12) United States Patent
Svensson et al.

(10) Patent No.: US 8,859,556 B2
(45) Date of Patent: Oct. 14, 2014

(54) TRPA1 RECEPTOR ANTAGONIST

(75) Inventors: Mats Svensson, Sodertalje (SE); Dirk Weigelt, Ronninge (SE)

(73) Assignee: Acturum Life Science AB, Solna (SE)

( * ) Notice: Subject to any disclaimer, the term of this patent is extended or adjusted under 35 U.S.C. 154(b) by 0 days.

(21) Appl. No.: 13/878,862

(22) PCT Filed: Oct. 11, 2011

(86) PCT No.: PCT/SE2011/051213
§ 371 (c)(1),
(2), (4) Date: Jun. 19, 2013

(87) PCT Pub. No.: WO2012/050512
PCT Pub. Date: Apr. 19, 2012

(65) Prior Publication Data
US 2014/0148466 A1    May 29, 2014

Related U.S. Application Data (60) Provisional application No. 61/392,130, filed on Oct. 12, 2010.

(51) Int. Cl.
*C07D 401/14* (2006.01)
*C07D 213/74* (2006.01)
*A61K 31/44* (2006.01)

(52) U.S. Cl.
USPC ..................... 514/253.01; 544/360

(58) Field of Classification Search
USPC ..................... 544/360; 514/253.01
See application file for complete search history.

(56) References Cited

U.S. PATENT DOCUMENTS

| | | | |
|---|---|---|---|
| 2009/0176883 A1 | 7/2009 | Perner et al. | |
| 2009/0325987 A1 | 12/2009 | Muthuppalniappan et al. | |

FOREIGN PATENT DOCUMENTS

| | | |
|---|---|---|
| WO | WO2005/012287 | 2/2005 |
| WO | WO2007/073505 | 6/2007 |
| WO | WO2008/007103 | 1/2008 |
| WO | WO2010/075353 | 7/2010 |

OTHER PUBLICATIONS

Bandell et al, "Noxious Cold Ion Channel TRPA1 Is Activated by Pungent Compounds and Bradykinin", Neuron 2004, 41(6), 849-857.
Bautista et al, "TRPA1 Mediates the Inflammatory Actions of Environmental Irritants and Proalgesic Agents", Cell 2006, 124(6), 1269-1282.
Jaquemar et al, "An Ankyrin-like Protein with Transmembrane Domains Is Specifically Lost after Oncogenic Transformation of Human Fibroblasts", J Biol Chem 1999, 274(11), 7325-7333.
Kremeyer et al, "A Gain-of-Function Mutation in TRPA1 Causes Familial Episodic Pain Syndrome", Neuron 2010, 66(5), 671-680.
Kwan et al, "TRPA1 Contributes to Cold, Mechanical, and Chemical Nociception but Is Not Essential for Hair-Cell Transduction", Neuron 2006, 50(2), 277-289.
McGaraughty et al, "TRPA1 modulation of spontaneous and mechanically evoked firing of spinal neurons in uninjured, osteoarthritic, and inflamed rats", Molecular Pain 2010, 6:14.
McNamara et al, "TRPA1 mediates formalin-induced pain", Proc Natl Acad Sci USA 2007, 104(33), 13525-13530.

*Primary Examiner* — Kahsay Habte
(74) *Attorney, Agent, or Firm* — Baker & Hostetler LLP

(57) ABSTRACT

A compound of Formula (I), pharmaceutically acceptable salts thereof, enantiomers, or mixtures thereof; pharmaceutical compositions containing said compounds, enantiomers or mixtures; processes for making said compounds, enantiomers or mixtures; the use of said compounds, enantiomers or mixtures; and medicaments containing the same for treatment of pain and other conditions; and methods of treating pain and other conditions with the same.

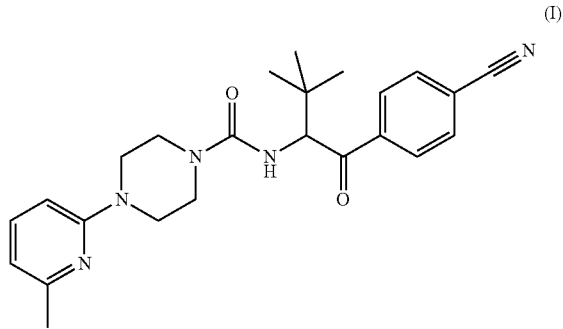

7 Claims, 2 Drawing Sheets

Abs.

VCD Experimental and Calculated Spectra.

TRPA1 RECEPTOR ANTAGONIST

FIELD OF THE INVENTION

The present invention relates to antagonists of the transient receptor potential (TRP) family of ion channels. The present invention also provides compositions comprising such antagonists and methods therewith for treating diseases mediated by the transient receptor potential (TRP) family of ion channels. Particularly, the present invention is related to non-selective cation channel TRPA1 antagonist compounds useful for treating pain and other specific disorders.

BACKGROUND

The transient receptor potential (TRP) family of ion channels are often found to be sensors of multiple chemical and physical stimuli (temperature, smell, taste and noxious chemicals). Particularly, the non-selective cation channel TRPA1 (transient receptor potential ankyrin-repeat 1), originally cloned as an ankyrin-like protein (Jaquemar et al 1999, J Biol Chem 274:7325-7333), is activated by multiple pungent and pro-algesic compounds (Bandell et al 2004, Neuron 41: 849-857). Recent reviews on TRPA1 as pharmaceutical target have been published by Rech et al. (Future Med. Chem. 2010: 843-838) and by Baraldi et al (J. Med. Chem. 2010, 5085-2107). TRPA1 is highly expressed in a subset of C-fiber nociceptors in the peripheral nerve system (Kobayashi et al 2005, J Comp Neurol 493(4):596-606). When activated TRPA1 permits the conduction of cations (primarily $Ca^{2+}$ and $Na^+$) from the extra cellular environment into the cell, thereby depolarizing the membrane potential and affecting calcium homeostasis in the primary afferents. Depolarization primary nerve terminals lead to action potential firing and consequently increased pain sensation and hyperalgesia in man and rodent experimental models (Jiang and Gebhart 1998, Pain 77(3):305-13; Cervero and Laird 1996, Pain 68(1):13-23). The pungent ingredient in mustard oil: allyl isothiocyanate (AITC), concentration dependently activates TRPA1 in vitro measured both on sodium current and calcium influx. Further, AITC also excites small diameter afferent fibers (Reeh 1986, Brain Res 384:42-50) and indeed topical application of AITC induces pain and hyperalgesia in man (Namer et al 2005, Neuroreport 16(9):955-959). Recently TRPA1 knock out (KO) mice were described to have lost AITC sensitivity and display severely impaired bradykinin pain response signalling (Kwan 2006, Neuron 50(2):277-289; Bautista 2006, Cell 124(6):1269-1282). Formalin, which is a mixture of methanol, water and formaldehyde is a widely used rodent model for evaluating analgesic compounds in vivo. TRPA1 is activated by formaldehyde in vitro and recently it was shown that TRPA1 KO mice almost have their response to formalin/formaldehyde abolished (McNamara et al 2007, Proc Natl Acad Sci USA 104(33):13525-13530). A Hydra Biosciences proprietary compound (HC030031) is a TRPA1 antagonist in vitro and has been shown to alleviate the formalin induced pain behaviour in a dose dependant way (McNamara 2007, Proc Natl Acad Sci USA 104(33):13525-13530 and WO2007/073505 A2). An Abbott proprietary compound (US 2009/0176883 and McGaraughty et al., Molecular Pain 2010 6:14) with in vitro effect on TRPA1 showed to have in vivo effect in a rat osteoarthritis pain model as well as a number of Glenmark proprietary compounds (US 2009/0325987) showed in several in vivo pain models. It has also been shown that a mutation in TRPA1 causes FEPS ("Familial Episodic Pain Syndrome", Kremeyer et al, Neuron 2010, 66:671-680). It is therefore suggested that in vitro inhibition of the TRPA1 calcium and sodium influx will determine a compound's propensity to work as an analgesic in vivo. An object of the present invention is therefore to provide new, improved and useful analgesics.

SUMMARY OF THE INVENTION

Non-selective cation channel TRPA1 antagonists are described. The described antagonists can be used for treating pain and other conditions. Medical conditions which are mediated by TRPA1 antagonists include asthma, pertussis and nicotine addiction.

DETAILED DESCRIPTION OF THE INVENTION

The present invention thus provides new antagonists of the non-selective cation channel TRPA1. The new antagonists can be used for, amongst other things, treating pain. Further medical conditions which are mediated by TRPA1 antagonists include asthma, pertussis and nicotine addiction.

In a first aspect, the present invention provides a compound of Formula (I), a pharmaceutically acceptable salt thereof, enantiomer, or mixture thereof:

(I)

It will be understood that as a compound of the present invention contains one chiral centers, the compound may exist in, and be isolated as, enantiomeric forms, or as a racemic mixture. The present invention includes any possible enantiomers, racemates or mixtures thereof, of a compound of Formula (I). The optically active forms of the compound of the invention may be prepared, for example, by chiral chromatographic separation of a racemate, by synthesis from optically active starting materials or by asymmetric synthesis based on the procedures described thereafter.

One embodiment of the present invention is the (R) enantiomer of a compound of Formula (I) having the following structure:

It will also be understood that a compound of the present invention may exist in solvated, for example hydrated, as well as unsolvated forms. It will further be understood that the present invention encompasses all such solvated forms of the compound of the Formula (I).

Within the scope of the invention are also salts of the compound of the Formula (I). Generally, pharmaceutically acceptable salts of compound of the present invention may be obtained using standard procedures well known in the art, for example by reacting a sufficiently basic compound, for example an alkyl amine with a suitable acid, for example, HCl or acetic acid, to afford a physiologically acceptable anion. It may also be possible to make a corresponding alkali metal (such as sodium, potassium, or lithium) or an alkaline earth metal (such as a calcium) salt by treating a compound of the present invention having a suitably acidic proton, such as a carboxylic acid or a phenol with one equivalent of an alkali metal or alkaline earth metal hydroxide or alkoxide (such as the ethoxide or methoxide), or a suitably basic organic amine (such as choline or meglumine) in an aq medium, followed by conventional purification techniques.

In one embodiment, a compound of Formula (I) above may be converted to a pharmaceutically acceptable salt or solvate thereof, particularly, an acid addition salt such as a hydrochloride, hydrobromide, phosphate, acetate, fumarate, maleate, tartrate, citrate, methanesulphonate or p-toluenesulphonate.

A compound of the present invention is contemplated to be useful in therapy, especially for the therapy asthma, pertussis (persistent cough), nicotine addiction and of various pain conditions including, but not limited to, acute and chronic pain disorders including but not limited to widespread pain, localized pain, nociceptive pain, inflammatory pain, central pain, central and peripheral neuropathic pain, central and peripheral neurogenic pain, central and peripheral neuralgia, chronic tendinitis, low back pain, postoperative pain, peripheral neuropathy, visceral pain, pelvic pain, allodynia, anesthesia dolorosa, causalgia, dysesthesia, fibromyalgia, hyperalgesia, hyperesthesia, hyperpathia, ischemic pain, sciatic pain, pain associated with cystitis, including but not limited to interstitial cystitis, pain associated with multiple sclerosis, pain associated with arthritis, pain associated with osteoarthritis, pain associated with rheumatoid arthritis, and pain associated with cancer.

In use for therapy in a warm-blooded animal such as a human, a compound of the invention may be administered in the form of a conventional pharmaceutical composition by any route including orally, intramuscularly, subcutaneously, topically, intranasally, intraperitoneally, intrathoracically, intravenously, epidurally, intrathecally, transdermally, intracerebroventricularly and by injection into the joints.

In one embodiment of the invention, the route of administration may be intravenous, topical, intradermal or intramuscular.

The dosage will depend on the route of administration, the severity of the disease, age and weight of the patient and other factors normally considered by the attending physician, when determining the individual regimen and dosage level at the most appropriate for a particular patient.

The present invention provides the use of a compound of Formula (I) or a pharmaceutically acceptable salt or solvate thereof, as hereinbefore defined in the manufacture of a medicament for use in therapy.

In particular medical indications, the present invention provides the use of a compound of Formula (I) for the manufacture of a medicament for the treatment of asthma, pertussis (persistent cough), nicotine addiction and of various pain conditions such as acute and chronic pain disorders including but not limited to widespread pain, localized pain, nociceptive pain, inflammatory pain, central pain, central and peripheral neuropathic pain, central and peripheral neurogenic pain, central and peripheral neuralgia, chronic tendinitis, low back pain, postoperative pain, peripheral neuropathy, visceral pain, pelvic pain, allodynia, anesthesia dolorosa, causalgia, dysesthesia, fibromyalgia, hyperalgesia, hyperesthesia, hyperpathia, ischemic pain, sciatic pain, pain associated with cystitis, including but not limited to interstitial cystitis, pain associated with multiple sclerosis, pain associated with arthritis, pain associated with osteoarthritis, pain associated with rheumatoid arthritis, and pain associated with cancer.

The present invention further provides a compound of Formula (I) for the treatment of asthma, pertussis (persistent cough), nicotine addiction and of various pain conditions such as acute and chronic pain disorders including but not limited to widespread pain, localized pain, nociceptive pain, inflammatory pain, central pain, central and peripheral neuropathic pain, central and peripheral neurogenic pain, central and peripheral neuralgia, chronic tendinitis, low back pain, postoperative pain, peripheral neuropathy, visceral pain, pelvic pain, allodynia, anesthesia dolorosa, causalgia, dysesthesia, fibromyalgia, hyperalgesia, hyperesthesia, hyperpathia, ischemic pain, sciatic pain, pain associated with cystitis, including but not limited to interstitial cystitis, pain associated with multiple sclerosis, pain associated with arthritis, pain associated with osteoarthritis, pain associated with rheumatoid arthritis, and pain associated with cancer.

A further aspect of the invention is a method for the treatment of a subject suffering from any of the conditions discussed above, whereby an effective amount of a compound according to the Formula (I) above, or pharmaceutically acceptable salt or solvate thereof, is administered to a patient in need of such treatment.

Thus, the invention provides a method for treating the specific medical indications set out above, wherein an effective amount of a compound of Formula (I) or pharmaceutically acceptable salt or solvate thereof, is administered to a patient in need of such treatment.

The present invention also provides a compound of Formula (I) for use as a medicament in therapy.

In the context of the present specification, the term "therapy" also includes "prophylaxis" unless there are specific indications to the contrary. The term "therapeutic" and "therapeutically" should be construed accordingly. The term "therapy" within the context of the present invention further encompasses to administer an effective amount of a compound of the present invention, to mitigate either a pre-existing disease state, acute or chronic, or a recurring condition. This definition also encompasses prophylactic therapies for prevention of recurring conditions and continued therapy for chronic disorders.

The compounds of Formula (I) have activity as pharmaceuticals, in particular as inhibitors (antagonists) of TRPA1. More particularly, the TRPA1 inhibitors of the present invention are useful in therapy, especially for relief of various pain conditions such as acute and chronic pain disorders including but not limited to widespread pain, localized pain, nociceptive pain, inflammatory pain, central pain, central and peripheral neuropathic pain, central and peripheral neurogenic pain, central and peripheral neuralgia, chronic tendinitis, low back pain, postoperative pain, peripheral neuropathy, visceral pain, pelvic pain, allodynia, anesthesia dolorosa, causalgia, dysesthesia, fibromyalgia, hyperalgesia, hyperesthesia, hyperpathia, ischemic pain, sciatic pain, pain associated with cystitis, including but not limited to interstitial cystitis, pain associated with multiple sclerosis, pain associated with arthritis, pain associated with osteoarthritis, pain associated with rheumatoid arthritis, and pain associated with cancer.

A compound according to Formula (I) may also be used in treatment of ophthalmological disorders such as retinopathies, diabetic retinopathies and glaucoma and treatment of pain associated with such disorders.

The compounds according to Formula (I) may also be used for ophthalmic treatment or for use as counter-agent for "riot control agents" such as CS or CR and for treating subjects suffering from the effects of such agents by administering a therapeutically effective amount of a compound according to Formula (I).

For the above-mentioned therapeutic uses the dosage administered will, of course, vary with the compound employed, the mode of administration, the treatment desired and the disorder indicated. The daily dosage of the compound of the invention may be in the range from 0.05 mg/kg to 100 mg/kg.

The compound of formula (I) and pharmaceutically acceptable salts thereof may be used on their own but will generally be administered in the form of a pharmaceutical composition in which the formula (I) compound/salt (active ingredient) is in association with a pharmaceutically acceptable adjuvant, diluent or carrier. Conventional procedures for the selection and preparation of suitable pharmaceutical formulations are described in, for example, "Pharmaceuticals—The Science of Dosage Form Designs", M. E. Aulton, Churchill Livingstone, 1988.

Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition. The present invention also provides a pharmaceutical composition comprising a compound of formula (I) or a pharmaceutically acceptable salt thereof as hereinbefore defined, in association with a pharmaceutically acceptable adjuvant, diluent or carrier.

The invention further provides a process for the preparation of a pharmaceutical composition of the invention which comprises mixing a compound of formula (I) or a pharmaceutically acceptable salt thereof as hereinbefore defined with a pharmaceutically acceptable adjuvant, diluent or carrier.

The pharmaceutical compositions may be administered topically (e.g. to the skin) in the form, e.g., of creams, solutions or suspensions; or systemically, e.g. by oral administration in the form of tablets, capsules, syrups, powders or granules; or by parenteral administration in the form of solutions or suspensions; or by subcutaneous administration; or by rectal administration in the form of suppositories; or transdermally. For oral administration the compound of the invention may be admixed with an adjuvant or a carrier, for example, lactose, saccharose, sorbitol, mannitol; a starch, for example, potato starch, corn starch or amylopectin; a cellulose derivative; a binder, for example, gelatine or polyvinylpyrrolidone; and/or a lubricant, for example, magnesium stearate, calcium stearate, polyethylene glycol, a wax, paraffin, and the like, and then compressed into tablets. If coated tablets are required, the cores, prepared as described above, may be coated with a concentrated sugar solution which may contain, for example, gum arabic, gelatine, talcum and titanium dioxide. Alternatively, the tablet may be coated with a suitable polymer dissolved in a readily volatile organic solvent.

For the preparation of soft gelatine capsules, the compound of the invention may be admixed with, for example, a vegetable oil or polyethylene glycol. Hard gelatine capsules may contain granules of the compound using either the above-mentioned excipients for tablets. Also liquid or semisolid formulations of the compound of the invention may be filled into hard gelatine capsules.

Liquid preparations for oral application may be in the form of syrups or suspensions, for example, solutions containing the compound of the invention, the balance being sugar and a mixture of ethanol, water, glycerol and propylene glycol. Optionally such liquid preparations may contain colouring agents, flavouring agents, saccharine and/or carboxymethylcellulose as a thickening agent or other excipients known to those skilled in art.

The compound of the invention may also be administered in conjunction with other compounds used for the treatment of the above conditions.

In a further embodiment, a compound of the present invention, or a pharmaceutical composition or formulation comprising a compound of Formula (I) is administered concurrently, simultaneously, sequentially or separately with another pharmaceutically active compound or compounds selected from the following:

(i) antidepressants such as agomelatine, amitriptyline, amoxapine, bupropion, citalopram, clomipramine, desipramine, doxepin duloxetine, elzasonan, escitalopram, fluvoxamine, fluoxetine, gepirone, imipramine, ipsapirone, maprotiline, nortriptyline, nefazodone, paroxetine, phenelzine, protriptyline, ramelteon, reboxetine, robalzotan, sertraline, sibutramine, thionisoxetine, tranylcypromaine, trazodone, trimipramine, venlafaxine and equivalents and pharmaceutically active isomer(s) and metabolite(s) thereof.

(ii) atypical antipsychotics including for example quetiapine and pharmaceutically active isomer(s) and metabolite(s) thereof.

(iii) antipsychotics including for example amisulpride, aripiprazole, asenapine, benzisoxidil, bifeprunox, carbamazepine, clozapine, chlorpromazine, debenzapine, divalproex, duloxetine, eszopiclone, haloperidol, iloperidone, lamotrigine, loxapine, mesoridazine, olanzapine, paliperidone, perlapine, perphenazine, phenothiazine, phenylbutylpiperidine, pimozide, prochlorperazine, risperidone, sertindole, sulpiride, suproclone, suriclone, thioridazine, trifluoperazine, trimetozine, valproate, valproic acid, zopiclone, zotepine, ziprasidone and equivalents and pharmaceutically active isomer(s) and metabolite(s) thereof.

(iv) anxiolytics including for example alnespirone, azapirones, benzodiazepines, barbiturates such as adinazolam, alprazolam, balezepam, bentazepam, bromazepam, brotizolam, buspirone, clonazepam, clorazepate, chlordiazepoxide, cyprazepam, diazepam, diphenhydramine, estazolam, fenobam, flunitrazepam, flurazepam, fosazepam, lorazepam, lormetazepam, meprobamate, midazolam, nitrazepam, oxazepam, prazepam, quazepam, reclazepam, tracazolate, trepipam, temazepam, triazolam, uldazepam, zolazepam and equivalents and pharmaceutically active isomer(s) and metabolite(s) thereof.

(v) anticonvulsants including for example carbamazepine, clonazepam, ethosuximide, felbamate, fosphenyloin, gabapentin, lacosamide, lamotrogine, levetiracetam, oxcarbazepine, phenobarbital, phenyloin, pregabaline, rufinamide, topiramate, valproate, vigabatrine, zonisamide and equivalents and pharmaceutically active isomer(s) and metabolite(s) thereof.

(vi) Alzheimer's therapies including for example donepezil, rivastigmine, galantamine, memantine, and equivalents and pharmaceutically active isomer(s) and metabolite(s) thereof.

(vii) Parkinson's therapies including for example deprenyl, L-dopa, Requip, Mirapex, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase and equivalents and pharmaceutically active isomer(s) and metabolite(s) thereof.

(viii) migraine therapies including for example almotriptan, amantadine, bromocriptine, butalbital, cabergoline, dichloralphenazone, dihydroergotamine, eletriptan, frovatriptan, lisuride, naratriptan, pergolide, pizotiphen, pramipexole, rizatriptan, ropinirole, sumatriptan, zolmitriptan, zomitriptan, and equivalents and pharmaceutically active isomer(s) and metabolite(s) thereof.

(ix) stroke therapies including for thrombolytic therapy with eg activase and desmoteplase, abciximab, citicoline, clopidogrel, eptifibatide, minocycline, and equivalents and pharmaceutically active isomer(s) and metabolite(s) thereof.

(x) urinary incontinence therapies including for example darafenacin, falvoxate, oxybutynin, propiverine, robalzotan, solifenacin, tolterodine and equivalents and pharmaceutically active isomer(s) and metabolite(s) thereof.

(xi) neuropathic pain therapies including for example lidocain, capsaicin, and anticonvulsants such as gabapentin, pregabalin, and antidepressants such as duloxetine, venlafaxine, amitriptyline, klomipramine, and equivalents and pharmaceutically active isomer(s) and metabolite(s) thereof.

(xii) nociceptive pain therapies such as paracetamol, NSAIDs and coxibs, such as celecoxib, etoricoxib, lumiracoxib, valdecoxib, parecoxib, diclofenac, loxoprofen, naproxen, ketoprofen, ibuprofen, nabumeton, meloxicam, piroxicam and opioids such as morphine, oxycodone, buprenorfin, tramadol, and equivalents and pharmaceutically active isomer(s) and metabolite(s) thereof.

(xiii) insomnia therapies including for example agomelatine, allobarbital, alonimid, amobarbital, benzoctamine, butabarbital, capuride, chloral, cloperidone, clorethate, dexclamol, ethchlorvynol, etomidate, glutethimide, halazepam, hydroxyzine, mecloqualone, melatonin, mephobarbital, methaqualone, midaflur, nisobamate, pentobarbital, phenobarbital, propofol, ramelteon, roletamide, triclofos, secobarbital, zaleplon, zolpidem and equivalents and pharmaceutically active isomer(s) and metabolite(s) thereof.

(xiv) mood stabilizers including for example carbamazepine, divalproex, gabapentin, lamotrigine, lithium, olanzapine, quetiapine, valproate, valproic acid, verapamil, and equivalents and pharmaceutically active isomer(s) and metabolite(s) thereof. Such combination products employ the compound of this invention within the dosage range described herein and the other pharmaceutically active compound or compounds within approved dosage ranges and/or the dosage described in the publication reference.

Method of Preparation, Experimental Work
General Methods

All solvents used were analytical grade and commercially available anhydrous solvents were routinely used for reactions. Reactions were typically run under an inert atmosphere of nitrogen or argon.

$^1$H, $^{19}$F and $^{13}$C NMR spectra were recorded on a Varian Unity+400 NMR Spectrometer equipped with a 5 mm BBO probe-head with Z-gradients, or a Varian Gemini 300 NMR spectrometer equipped with a 5 mm BBI probe head, or a Bruker Avance 400 NMR Spectrometer equipped with a 60 µl dual inverse flow probe head with Z-gradients, or a Varian Mercury Plus 400 NMR Spectrometer equipped with a Varian 400 ATB PFG probe, or a Bruker DPX400 NMR spectrometer equipped with a 4-nucleus probe head equipped with Z-gradients, or a Bruker Avance 600 NMR spectrometer equipped with a 5 mm BBI probe head with Z-gradients. Unless specifically noted in the examples, spectra were recorded at 400 MHz for proton, 376 MHz for $^{19}$F and 100 MHz for $^{13}$C.

Alternatively, $^1$H and $^{13}$C NMR spectra were recorded at 400 MHz for proton and 100 MHz for $^{13}$C on a Varian Mercury Plus 400 NMR Spectrometer equipped with a Varian 400 ATB PFG probe.

The following reference signals were used: the middle line of DMSO-$d_6$ δ 2.50 (1H), δ 39.51 (13C); the middle line of CD$_3$OD δ 3.31 (1H) or δ 49.15 (13C); CDCl$_3$ δ 7.26 (1H) and the middle line of CDCl$_3$ δ 77.16 (13C) (unless otherwise indicated). NMR spectra are reported from low to high field. Alternatively, all deuterated solvents contained typically 0.03% to 0.05% v/v tetramethylsilane, which was used as the reference signal (set at δ 0.00 for both $^1$H and $^{13}$C).

Mass spectra were recorded on a Waters LCMS consisting of an Alliance 2795 (LC), Waters PDA 2996 and a ZQ single quadrupole mass spectrometer or Waters Micromass ZQ detector at 120° C. The mass spectrometer was equipped with an electrospray ion source (ESI) operated in a positive or negative ion mode. The capillary voltage was 3 kV and cone voltage was 30 V. The mass spectrometer was scanned between m/z 100-700 or m/z 100-1000 with a scan time of 0.3 s. Separations were performed on either Waters X-Terra MS C8 (3.5 µm, 50 or 100 mm×2.1 mm i.d.) or an ACE 3 AQ (100 mm×2.1 mm i.d.) obtained from ScantecLab. Flow rates were regulated to 1.0 or 0.3 mL/min, respectively. The column temperature was set to 40° C. A linear gradient was applied using a neutral or acidic mobile phase system, starting at 100% A (A: 95:5 10 mM NH$_4$OAc:MeCN, or 95:5 8 mM HCOOH:MeCN) ending at 100% B (MeCN).

Mass spectra also were recorded on a Waters LCMS consisting of an Alliance 2690 Separations Module, Waters 2487 Dual 1 Absorbance Detector (220 and 254 nm) and a Waters ZQ single quadrupole mass spectrometer. The mass spectrometer was equipped with an electrospray ion source (ESI) operated in a positive or negative ion mode. The capillary voltage was 3 kV and cone voltage was 30 V. The mass spectrometer was scanned between m/z 97-800 with a scan time of 0.3 or 0.8 s. Separations were performed on a Chromolith Performance RP-18e (100×4.6 mm). A linear gradient was applied starting at 95% A (A: 0.1% HCOOH (aq.)) ending at 100% B (MeCN) in 5 min. Flow rate: 2.0 mL/min.

Alternatively, Ultra Pressure (UP) LCMS analyses were performed on an Waters Acquity UPLC system consisting of a Acquity Autosampler, Acquity Sample Organizer, Acquity Column Manager, Acquity Binary Solvent Manager, Acquity UPLC PDA detector and a Waters SQ Detector. The mass spectrometer was equipped with an electrospray ion source (ES) operated in positive and negative ion mode. The capillary voltage was set to 3.0 kV and the cone voltage to 30 V, respectively. The mass spectrometer was scanned between m/z 100-600 with a scan time of 0.105 s. The diode array detector scanned from 200-400 nm. The temperature of the Column Manager was set to 60° C. Separation was performed on a Acquity column, UPLC BEH, C18 1.7 µM run at a flow rate of 0.5 mL/min. A linear gradient was applied starting at 100% A (A: 10 mM NH$_4$OAc in 5% MeCN) ending at 100% B (B: MeCN) after 1.3 min then 100% B for 0.6 min. ESpos/ESneg, m/z 100-600.

Compound identification was also performed on a GC-MS system supplied by Agilent Technologies, consisting of a 6890N G1530N GC, a G2614A Autosampler, G2613A injector and a G2589N mass spectrometer. The column used was a VF-5 MS, ID 0.25 mm×30 m, 0.25 µm (Varian Inc.). A linear temperature gradient was applied starting at 70° C. (hold 1 min) and ending at 300° C. (hold 1 min), 25° C./min. The mass spectrometer was equipped with a chemical ionisation (CI) ion source and the reactant gas was methane. The mass spectrometer scanned between m/z 50-500 and the scan speed was set to 3.21 scan/s. Solvent delay was set from 0 min to 2.0 min.

HPLC analyses were performed on an Agilent HP1000 system consisting of G1379A Micro Vacuum Degasser, G1312A Binary Pump, G1367A Well plate autosampler, G1316A Thermostatted Column Compartment and G1315B Diode Array Detector. Column: X-Terra MS, Waters, 3.0× 100 mm, 3.5 μm. The column temperature was set to 40° C. and the flow rate to 1.0 mL/min. The Diode Array Detector was scanned from 210-300 nm, step and peak width were set to 2 nm and 0.05 min, respectively. A linear gradient was applied, starting at 100% A (A: 95:5 10 mM NH$_4$OAc: MeCN) and ending at 100% B (B: MeCN), in 4 min.

HPLC analyses were also performed with a Gynkotek P580 HPG consisting of gradient pump with a Gynkotek UVD 170S UV-vis.-detector equipped with a Chromolith Performance RP column (C18, 100 mm×4.6 mm). The column temperature was set to 25° C. A linear gradient was applied using MeCN/0.1 trifluoroacetic acid in MilliQ water, run from 10% to 100% MeCN in 5 min. Flow rate: 3 mL/min.

Chiral purity analysis was run on a SFC Berger Analytix system with Agilent 1100 PDA detector. The column temperature was set to 50° C. An isocratic condition a mixture of EtOH and CO$_2$ was applied at flow rate 2.0 mL/min. The PDA was scanned from 190-600 nm and 220 nm was extracted for purity determination.

Chiral HPLC analyses were alternatively performed on a Gilson chiral system Column: Chiralpak AD-H, 4.6*250 mm; 5 μm Mobile phase: 100% EtOH Flow rate: 0.8 mL/min. Optical rotation was determined with a PDR-Chiral laser polarimeter. Microwave heating was performed in a single-mode microwave cavity producing continuous irradiation at 2450 MHz.

Thin layer chromatography (TLC) was performed on Merck TLC-plates (Silica gel 60 F$_{254}$) and UV visualized the spots.

Flash chromatography was performed on a Combi Flash® Companion™ using RediSep™ normal-phase flash columns or using Merck Silica gel 60 (0.040-0.063 mm). Typical solvents used for flash chromatography were mixtures of chloroform/methanol, dichloromethane/methanol, heptane/ethyl acetate, chloroform/methanol/ammonia (aq.) and dichlorormethane/methanol/NH$_3$ (aq.).

Preparative chromatography was run on a Waters auto purification HPLC with a diode array detector. Column: XTerra MS C8, 19×300 mm, 10 μm. Narrow gradients with MeCN/ (95:5 0.1M NH$_4$OAc:MeCN) were used at a flow rate of 20 mL/min.

Purification was also achieved on a semi preparative Shimadzu LC-8A HPLC with a Shimadzu SPD-10A UV-vis.-detector equipped with a Waters Symmetry® column (C18, 5 μm, 100 mm×19 mm). Narrow gradients with MeCN/0.1% trifluoroacetic acid in MilliQ Water were used at a flow rate of 10 mL/min.

Alternatively, purification was achieved on a preparative Gilson 281 (Gilson Pump 322) HPLC with a Gilson 156 UV-detector equipped with a Waters Sunfire column (150 mm×21.2 mm). Narrow gradients with MeCN/0.1% formic acid in water were used at a flow rate of 15 mL/min.

Chiral preparative chromatography was run on a SFC Berger Multigram system with a Knauer K-2501 UV detector. The column temperature was set to 35° C. An isocratic condition of a mixture of EtOH and CO$_2$ was applied at flow rate 50.0 mL/min. The UV detector scanned at 220 nm. The UV signal determined the fraction collection.

Compounds have been named using either ACD/Name, version 10.06, software from Advanced Chemistry Development, Inc. (ACD/Labs), Toronto ON, Canada, www.acdlabs.com, or Lexichem, version 1.4, software from OpenEye.

ABBREVIATIONS

Abs Absorption
aq aqueous
CAS Chemical Abstracts Service
CDI 1,1'-carbonyldiimidazole
DCM dichloromethane
DIPEA N,N-diisopropylethylamine
DMF dimethylformamide
DMSO dimethyl sulfoxide
EDCI 1-ethyl-3-(3-dimethylaminopropyl) carbodiimide
ES electro spray
ESI electro spray ionization
eq equivalent(s)
GC gas chromatography
h hour(s)
HCl hydrochloric acid, hydrochloride
HPLC high-performance liquid chromatography
IPC In-process control
M Molar (moles per liter)
min minute(s)
MS mass spectrometry
NMR nuclear magnetic resonance
prep. Preparative
rt room temperature
Rt retention time
SFC Supercritical fluid chromatography
T$_j$ Jacket temperature
T$_i$ Internal temperature
TEA triethylamine
TLC thin layer chromatography
THF tetrahydrofuran
TLC thin layer chromatography
UV ultraviolet
VCD Vibrational Circular Dichroism
Starting Materials Example 1 tert-Butyl 1-(methoxy(methyl)amino)-3,3-dimethyl-1-oxobutan-2-ylcarbamate

Method 1

To a solution of 2-(tert-butoxycarbonylamino)-3,3-dimethylbutanoic acid (CAS 102185-35-3, 500 mg, 2.16 mmol) in DCM (5 mL) was added EDCI (CAS 25952-53-8, 497 mg, 2.59 mmol) and stirred for 10 min at rt. A solution of N,O-dimethylhydroxylamine hydrochloride (CAS 6638-79-5, 253 mg, 2.59 mmol) and DIPEA (0.429 mL, 2.59 mmol) in DCM (5 mL) was added and the reaction mixture was left to stir at rt over a weekend. The mixture was diluted with DCM (30 mL) and extracted with saturated aq NaHCO₃ (50 mL). The organic phase was washed with water before being dried over MgSO₄ and filtered. The solvent was removed in vacuo to give tert-butyl 1-(methoxy(methyl)amino)-3,3-dimethyl-1-oxobutan-2-ylcarbamate (466 mg, 79%).

$^1$H NMR (500 MHz, CDCl₃) δ ppm 0.98 (s, 9H) 1.43 (s, 9H) 2.19-2.28 (m, 1H) 3.21 (s, 3H) 3.78 (s, 3H) 4.66 (d, 1H). GC-MS (unprotected amino acid) m/z 130, Rt: 5.82 min.

Method 2

To a cleaned and dried 10 L reactor at $T_j$ 25° C. was charged N-boc-tert-butylglycin (N-Boc-tert-Leucine, CAS 102185-35-3) (188 g; 0.77 mol; 1.00 eq) and DCM (6.25 L; 35 vol) giving a fine slurry. 1,1'-Carbonylimidazole (208.7 g; 1.3 eq) was added under stirring in one portion affording a clear pale green solution after approx 1 min under gas exhaust. The reaction was monitored by GC and after 1 h rt at $T_j$ 25° C. a second portion of 1,1'-carbonylimidazole (32.1 g; 0.2 eq) was added and the reaction mixture was left overnight. To the clear reaction mixture N,O-dimethylhydroxylamine (153.7 g; 2.0 eq) was added followed by TEA (215 mL; 2.0 eq). $T_j$ was set to 50° C. and the reaction conversion was followed by GC analyses. A second portion of N,O-dimethylhydroxylamine (26.9 g; 0.35 eq) and TEA (37 mL; 0.35 eq) was added to the mixture and the reaction was left for 48 h at $T_j$ 50° C. ($T_i$ 41° C.) giving a conversion of 98.7%. The reaction mixture (approx pH 8) was cooled and at $T_j$ 20° C. water (2.82 L; 15 vol) was charged to the reactor and the resulting mixture was stirred for 10 min. The organic layer was recovered and washed twice with water (2×2.82 L; 2×15 vol), NaHCO₃ (2×2.3 L; 2×12 vol) and finally with water (2×1.88 L; 2×10 vol). The organic layer was concentrated in vacuo at 40° C. giving a yellow residual oil, which was co-evaporated with toluene (250 mL) giving 295 g oily product and left overnight. A crystalline mixture appeared. The mixture was filtered (P3 sintered disk; 100 mm diameter), washed with toluene (75 mL) and dried affording 138 g of white crystalline material. A second crop (158 g) was obtained, dissolved in hot n-heptane (250 mL) cooled with an external ice-water bath giving 56 g of pale colored material. Analyses gave of first crop 96.8% w/w and of second crop 72% w/w respectively. Total yield (194 g) based on NMR assays was 82%.

Example 2a tert-Butyl 1-(4-chlorophenyl)-3,3-dimethyl-1-oxobutan-2-ylcarbamate tert-Butyl 1-(methoxy(methyl)amino)-3,3-dimethyl-1-oxobutan-2-ylcarbamate (Example 1, 466 mg, 1.70 mmol) was dissolved in dry THF (10 mL). (4-Chlorophenyl)magnesium bromide (CAS 873-77-8, 1.0 M in THF, 6.79 mL, 6.79 mmol) was then added dropwise at rt. After stirring at rt overnight the reaction was quenched with NH₄Cl and extracted with EtOAc (2×50 mL). The combined organic phases were washed once with water, dried over MgSO₄ and filtered. After removal of the solvent the product was purified on a silica gel column eluted with heptane:EtOAc 10-20% to give tert-butyl 1-(4-chlorophenyl)-3,3-dimethyl-1-oxobutan-2-ylcarbamate (137 mg, 25%).

$^1$H NMR (500 MHz, CDCl₃) δ ppm 0.93 (s, 9H) 1.44 (s, 9H) 5.12 (d, 1H) 5.40 (d, 1H) 7.46 (d, 2H) 7.95 (d, 2H). MS (ESI) m/z 325.8 [M+H]⁺.

Example 2b tert-Butyl 1-(4-cyanophenyl)-3,3-dimethyl-1-oxobutan-2-ylcarbamate

To a dried and cleaned 10 L cryo reactor was added 4-bromobenzonitrile (321 g; 1.74 mol; 2.5 eq) and THF (995 mL; 5.0 vol). The stirred mixture was inerted under a nitrogen atmosphere and cooled ($T_j$ –20° C.). To the cooled mixture at $T_j$ –13° C. Turbo Grignard reagent (Turbo Grignard Reagent from Chemetall equal to iPrMgCl/LiCl 14% w/w in THF; 1.81 L; 2.5 eq) was charged under the nitrogen atmosphere while maintaining the temperature below approx –10° C. during 1 h 14 min. The reaction intermediate was left at approx 0° C. for 3 h giving a conversion of >97% (analytical sample quenched with 15% w/w aq NH₄Cl). The mixture was cooled to $T_i$ –20° C. and a solution of tert-butyl 1-(methoxy(methyl)amino)-3,3-dimethyl-1-oxobutan-2-ylcarbamate (191 g; 0.70 mol; 1.0 eq) in THF 496 mL; 2.6 vol) was charged to the reactor for 28 min at approx-10° C. to –6° C. (exothermal reaction). The vessel was rinsed with THF (221 mL; 1.3 L), the reaction mixture warmed to 20° C. and left overnight affording a conversion (HPLC) of approx 90%. The mixture was cooled to 0° C. ($T_j$-10) and a solution of potassium sodium tartrate (Rochelle salt) (153 g; 1.05 eq) in water (10 vol) was drop wise added during 30 min keeping the temperature at 0 to 10° C. giving an orange coloured slurry. $T_j$ was set to 40° C. and stirring was stopped at $T_i$ 30° C. and the phases allowed to separate. The red coloured organic layer was recovered and the yellow slurry-like water phase was extracted twice at $T_j$ 30° C. with iPrOAc (2×1.91 L; 2×10 vol). The organic layers were combined (7.5 L) and washed at $T_j$ 30° C. three times with a brine-water mixture (3+3 vol; 5+5 vol; 3+3 vol). The washed organic layer was concentrated in vacuo at $T_j$ 60° C. to approx 1.5 L volume and diluted (iPrOAc) to 2 L. The product solution was taken to the next step (example 3, method 2) without further purification.

Example 3

4-(2-Amino-3,3-dimethylbutanoyl)benzonitrile hydrochloride

Method 1 tert-Butyl 1-(4-chlorophenyl)-3,3-dimethyl-1-oxobutan-2-ylcarbamate (Example 2a, 2.30 g, 7.06 mmol) and Zn(CN)₂ (0.87 g, 7.4 mmol) were dissolved in DMF (20 mL) under N2 (g). Pd(PPh₃)₄ (0.86 g, 0.74 mmol) was added and the mixture was heated at 130° C. overnight. The mixture was cooled to rt, diluted with water and extracted with EtOAc. The organic phase was washed with brine, dried over Na₂SO₄ and evaporated. The product was purified on a silica column (EtOAc: hexane 1:10) to give tert-butyl 1-(4-cyanophenyl)-3,3-dimethyl-1-oxobutan-2-ylcarbamate (961 mg, 43%). tert-Butyl 1-(4-cyanophenyl)-3,3-dimethyl-1-oxobutan-2-ylcarbamate (961 mg, 3.04 mmol) was dissolved in 1.25 M HCl in MeOH at 0° C. and the mixture was stirred at rt for 8 h. The solvent was removed and the residue dried in vacuo to give 4-(2-amino-3,3-dimethyl-butanoyl)-benzonitrile hydrochloride (110 mg, 93%).

¹H NMR (400 MHz, MeOD) δ ppm 1.02 (s, 9H) 5.05 (s, 1H) 7.96 (d, 2H) 8.20 (d, 2H). MS (ESI) m/z 217.1 [M+H]⁺

Method 2

To a cleaned and dried 10 L reactor at $T_j$ 65° C. was charged 2-propanol (573 mL) and HCl in 2-propanol (5 M; 696 mL; 5 eq). To the mixture at $T_i$ 53° C. was added portion-wise (approx 150 mL) the solution tert-butyl 1-(4-cyanophenyl)-3,3-dimethyl-1-oxobutan-2-ylcarbamate from the previous stage (Example 2b as described above) during 9 min (after approx 600 mL charging the product starts to precipitated out). The slurry was stirred for 1 h and analyses gave complete conversion (GC). The fine crystalline slurry was cooled ($T_j$ 0° C.) and left overnight.

The product was isolated on glass filters (2 filters; P3 sintered disk; 130 mm diameter) in vacuo (slow filtration during approx 3 h). The product was displacement-washed in each filter with a mixture of cold (0° C.) 2-propanol (496 mL; 2.6 vol) and iPrOAc (650 mL; 3.4 vol) and with MeTHF (2×425 mL; 2×3 vol). The product was dried in vacuo 40° C. over a weekend giving 135 g of white fine crystalline hydrochloric acid salt. Analyses gave a HPLC purity of 99.5 area-% (254 nm) and a NMR assay of 94% w/w. Yield 72% based on NMR assay over two stages.

Example 4

1-(6-Methylpyridin-2-yl)piperazine

To a cleaned and dried ½ L round-bottom flask was added 2-chloro-6-methylpyridine (80 g; 620 mmol; 1.0 eq) and piperazine (400 g; 7.40 eq). The mixture was heated using an external oil bath ($T_j$ 154° C.) and magnetically stirred. After approx 6 h reaction time the reaction was considered to be complete (GC analyses) and allowed to cool to room temperature. To the cold mixture was added toluene (475 mL; 6 vol) and water (633 mL; 8 vol) giving two clear phases. The water phase was recovered and extracted with toluene (150 mL). The toluene layers were combined, washed with brine (17.5% w/w; 150 mL) and concentrated in vacuo to give an oily residue (estimated amount 88 g free base). To a 1 L reactor at room temperature was added a solution of free base dissolved in MeTHF (790 mL; 10 vol) to an aq HCl solution (1N; 396 mL; 5 eq). The yellow water phase was recovered and cooled with an external ice-water bath and basified to pH>11 with NaOH (5M; 95 mL). The basic aq phase was extracted with MeTHF (792 mL; 10 vol), the water phase was recovered and the organic layer was concentrated in vacuo and dried by azeotropic distillation. The dried MeTHF product-containing layer (470 mL; 5 vol) was cooled with an external ice-water bath giving an opaque solution. To the solution was slowly added HCl in 2-propanol (310 mL, 3.0 eq) and an off-white product precipitated out. The obtained slurry was cooled for 1 h and the product was isolated on a glass filter (P3 sintered disk 100 mm diameter), washed with ice-cold MeTHF (100 mL). The product was dried in vacuo at 40° C. to give 101 g as a di-hydrochloride salt (65%). The purity was determined on GC giving 96.7 area-% and the NMR assay was 71.5% w/w (base). Yield 75% based on NMR assay.

Final Compounds

Example 5

N-(1-(4-Cyanophenyl)-3,3-dimethyl-1-oxobutan-2-yl)-4-(6-methylpyridin-2-yl)piperazine-1-carboxamide Method 1

4-(2-Amino-3,3-dimethylbutanoyl)benzonitrile hydrochloride (Example 3, 50 mg, 0.23 mmol) was added to a solution of CDI (112 mg, 0.69 mmol) and TEA (0.035 mL, 0.25 mmol) in MeCN (5 mL). The reaction mixture was stirred at rt for 90 minutes before 1-(6-methylpyridin-2-yl)piperazine (CAS 55745-89-6, 205 mg, 1.16 mmol) was added. The mixture was stirred for 1 h and the solvent was evaporated under reduced pressure. The product was dissolved in methanol, filtered and purified by prep. HPLC yielding N-(1-(4-cyanophenyl)-3,3-dimethyl-1-oxobutan-2-yl)-4-(6-methylpyridin-2-yl)piperazine-1-carboxamide (36.3 mg, 37%).

¹H NMR (400 MHz, CDCl₃) δ ppm 0.94 (s, 9H) 2-40 (s, 3H) 3.48-3-68 (m, 8H) 5.25-5-31 (m, 1H) 5.33-5.39 (m, 1H) 6.43 (d, 1H) 6.53 (d, 1H) 7.40 (dd, 1H) 7.78 (m, 2H) 8.14 (m, 2H). MS (ESI) m/z 418.3 [M–H]⁻

Method 2

Bis(trichloromethyl)carbonate (60.6 mg, 0.20 mmol) was added portion-wise to 4-(2-amino-3,3-dimethylbutanoyl)benzonitrile hydrochloride (Example 3, 129 mg, 0.51 mmol) and TEA (0.285 mL, 2.04 mmol) in DCM (2 mL) under 1 minute at rt. After stirring for 20 min, a solution of 1-(6-methylpyridin-2-yl)piperazine (CAS 55745-89-6, 90 mg, 0.51 mmol) and TEA (0.142 mL, 1.02 mmol) in DCM (2 mL) was added drop-wise and the reaction was stirred for 90 min. The volatiles were removed before the reaction mixture was diluted with MeOH, filtered and purified by preparative HPLC. Fractions were pooled and freeze-dried to give N-(1-(4-cyanophenyl)-3,3-dimethyl-1-oxobutan-2-yl)-4-(6-methylpyridin-2-yl)piperazine-1-carboxamide (76 mg, 36%).

¹H NMR (500 MHz, MeOD) δ ppm 0.99 (s, 9H) 2.36 (s, 3H) 3.53 (m, 8H) 5.30 (m, 1H) 6.34 (m, 1H) 6.57 (t, 3H) 7.44 (dd, 1H) 7.88 (m, 2H) 8.17 (m, 2H). MS (ESI) m/z 420.2 [M+H]⁺

Method 3

To a cleaned and dried 10 L reactor at $T_j$ 22° C. was added CDI (153.7 g; 0.74 mol; 1.5 eq) followed by DMF (1 L; 8.0 vol) giving a clear pale yellow solution. To the solution above was added at $T_j$ 22° C., 10 portions of a pre-made suspension/solution of 4-(2-amino-3,3-dimethylbutanoyl)benzonitrile×HCl (Example 3 prepared by method 2; 135 g; 0.50 mol; 1.0 eq), DMF (1 L; 8.0 vol) and TEA (127 g; 1.26 mol) during 30 min. The temperature was increased to 25° C. and the resulting mixture was stirred for 30 min. An IPC was taken (GC) to give full conversion of starting material to imidazole urea intermediate. $T_j$ was set to 5° C. and TEA (247.5 g; 5 eq) was added to the reaction mixture <10° C. To the mixture was added during 33 min portion-wise 1-(6-methylpyridin-2-yl)piperazine×2HCl (Example 4; 184 g; 1.50 eq) maintaining the inner temperature <30° C. The reaction mixture was stirred for another 30 min at $T_j$ 25° C. and an IPC was taken giving a conversion of 99.5% (HPLC). The mixture was cooled ($T_j$ 5° C.) and left overnight. To the mixture at 5° C. was added in portions an aq solution of $NH_4Cl$ (285 g; 10 eq) in water (2.0 L; 15 vol) during 8 min. The $T_j$ was set to 25° C. and to the resulting mixture was added toluene (2.26 L; 16.7 vol). The organic phase was recovered and the water phase was extracted once with toluene (2.26 L; 16.7 vol). The organic phases were combined, washed with water (500 mL; 3.7 vol) and extracted twice with a solution of 2× HCl (30% w/w; 127 mL; 2 eq) in water (2.5 L; 18.5 vol). The acid water phase was washed with toluene (1.1 L; 8.1 vol). The organic layer was recovered and the water phase was recharged to the reactor and EtOAc (2.3 L; 17 vol) was added. To the mixture at 25° C. was added a pre-made aq solution of $NaHCO_3$ (249 g; 5.9 eq) in water (pH 8) under stirring. The basic aq phase was recovered, washed with EtOAc (2.2 L; 16 vol), organic phases were combined and washed with brine (400 mL) and the solution left overnight at $T_j$ 15° C. The organic layer (4 L) was concentrated in vacuo at 40° C. to approx half volume, mixed with $SiO_2$ (approx 250 g) and the solvent was removed to give a silica powder column head. The silica column head was placed on a pre-packed silica column with EtOAc (120 mm×400 mm; approx 4 kg $SiO_2$ 40-60 mesh). The flash chromatography procedure used approx 20 L EtOAc as eluent and the process was monitored by TLC. Fractions (approx 250 mL) were pooled after TLC analyses and concentrated in vacuo at 40° C. The obtained product was dried in vacuo at 40° C. to give 191.5 g of pure white material. Analyses gave a HPLC purity of 99.7 area-% (254 nm) and an assay of 98.5% w/w. Residual solvent EtOAc 0.1% w/w. This material (180 g) was used for preparation of the desired enantiomer, N-(1-(4-cyanophenyl)-3,3-dimethyl-1-oxobutan-2-yl)-4-(6-methylpyridin-2-yl)piperazine-1-carboxamide. Yield 90% based on NMR assay (calculated).

Example 6

(R)—N-(1-(4-Cyanophenyl)-3,3-dimethyl-1-oxobutan-2-yl)-4-(6-methylpyridin-2-yl)piperazine-1-carboxamide Method 1

19 mg of the racemate from Example 5 was separated by chiral chromatography to yield ((R)—N-(1-(4-cyanophenyl)-3,3-dimethyl-1-oxobutan-2-yl)-4-(6-methylpyridin-2-yl)piperazine-1-carboxamide) (5.6 mg, 30%).

Chiral purity 100%, Rt 4.42 min on the following system: SFC Berger Analytix, Column: Chiralcel OD-H, 4.6*250 mm; 5 µm, mobile phase: 20% EtOH; 80% $CO_2$, flow: 2 mL/min.

$^1$H NMR (500 MHz, DMSO-$d_6$) δ ppm 0.93 (s, 9H) 2.29 (s, 3H) 3.43 (m, 8H) 5.11 (d, 1H) 6.52 (d, 1H) 6.59 (m, 2H) 7.42 (dd, 1H) 7.98 (d, 2H) 8.14 (d, 2H). MS (ESI) m/z 420.3 [M+H]$^+$

Method 2

Chiral preparative chromatography was used to prepare Example 6 using a high pressure preparative chromatographic system.

The racemate was solubilised in ethanol (25 g/L feed solution). The stationary phase was Chiralcel OD (20 micron) and the mobile phase was isoHexane/ethanol 90:10. The separation was carried out at a temperature of 25° C., 30 mL of feed (0.75 g) was loaded onto the column per injection. The injections were stacked every 15 minutes to increase the efficiency of the separation at a flow rate of 120 mLs/min. A UV detection wavelength of 320 nm was used. A single fraction (1st eluting peak) was collected, periodically the fractions taken were analysed on a HPLC using the following conditions. Chiralcel OD-H, 4.6*250 mm; 5 µm, mobile phase 60:40 IsoHexane/IPA 1 ml/min RT≈8.3 minutes. Final chiral purity 100%. Yield≈45%.

Example 7

(S)—N-(1-(4-Cyanophenyl)-3,3-dimethyl-1-oxobutan-2-yl)-4-(6-methylpyridin-2-yl)piperazine-1-carboxamide 19 mg of the racemate from Example 5 was separated by chiral chromatography to yield (S)—N-(1-(4-cyanophenyl)-3,3-dimethyl-1-oxobutan-2-yl)-4-(6-methylpyridin-2-yl)piperazine-1-carboxamide (4.2 mg, 22%).

Chiral purity 99.8%, Rt 6.34 min on the following system: SFC Berger Analytix, Column: Chiralcel OD-H, 4.6*250 mm; 5 µm, mobile phase: 20% EtOH; 80% $CO_2$, flow: 2 mL/min.

$^1$H NMR (500 MHz, DMSO-$d_6$) δ ppm 0.94 (s, 9H) 2.29 (s, 3H) 3.42 (m, 8H) 5.12 (d, 1H) 6.52 (d, 1H) 6.60 (dd, 2H) 7.42 (dd, 1H) 7.99 (m, 2H) 8.15 (m, 2H). MS (ESI) m/z 420.3 [M+H]$^+$ Solid State Characterisation (R)—N-(1-(4-Cyanophenyl)-3,3-dimethyl-1-oxobutan-2-yl)-4-(6-methylpyridin-2-yl)piperazine-1-carboxamide (example 6)

X-Ray Powder Diffraction (XRPD) patterns were collected on a PANalytical X'Pert PRO MPD theta-theta system using long-fine-focus Cu Kα-radiation, wavelength of X-rays 1.5418 Å, at 45 kV and 40 mA. A programmable divergence slit and a programmable anti-scatter slit giving an irradiated length of 10 mm were used. 0.02 radian Soller slits were used on the incident and on the diffracted beam path. A 20 mm fixed mask was used on the incident beam path and a Nickel-filter was placed in front of a PIXcel-detector using 255 active channels. Thin flat samples were prepared on flat silicon zero background plates using a spatula. The plates were mounted in sample holders and rotated in a horizontal position during measurement. Diffraction patterns were collected between 2° 2theta and 40° 2theta in a continuous scan mode. Total time for a scan between 2 and 40° 2theta was approximately 10 minutes.

Figure 1:
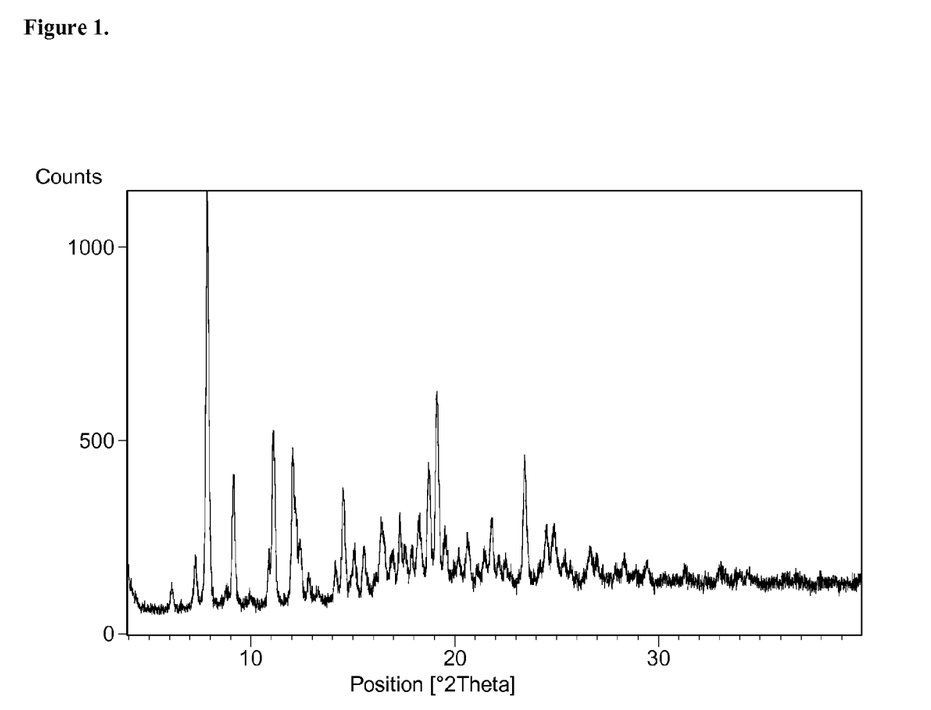
FIG. 1 shows an X-Ray Powder Diffraction (XRPD) pattern for the compound of Example 6.

A diffractogram for (R)—N-(1-(4-cyanophenyl)-3,3-dimethyl-1-oxobutan-2-yl)-4-(6-methylpyridin-2-yl)piperazine-1-carboxamide is shown in FIG. 1.

Vibrational Circular Dichroism
Computational Spectral Simulations:

A Monte Carlo molecular mechanics search for low energy geometries was conducted for the S enantiomer fragment (II) using MacroModel within the Maestro graphical interface (Schrödinger Inc.). All conformers within 5 kcal/mole of the lowest energy conformer were used as starting points for density functional theory (DFT) minimizations within Gaussian03.

(II)—Fragment for which VCD calculations were performed

Optimized structures, harmonic vibrational frequencies/intensities, VCD rotational strengths, and free energies at STP (including zero-point energies) were determined for each conformer. In these calculations, the B3PW91 generalized gradient approximation (GGA) exchange-correlation density functional was used in conjunction with the 6-31G* basis set. Simulation of VCD spectra for each conformation were generated and fit to Lorentzian line shapes (12 cm$^{-1}$ line width), and the computed spectra were Boltzmann-weighted to allow direct comparisons between simulated and experimental spectra.

VCD Experimental:

The experimental spectra were obtained by dissolving ~8 mg of sample in ~0.15 mL of CDCl$_3$. Analyses were conducted at 4 cm$^{-1}$ resolution in a 0.1 mm BaF$_2$ cell using the dual source, dual PEM, VCD scan protocol using the BioTools ChiralIR instrument. The instrument incorporated a dual photo-elastic modulator set for polarization modulation at 37.024 kHz with λ/4 retardation (optimized for acquisition of the spectral region centered around 1300 cm$^{-}$). Lock-in amplification with a 30 μs time constant, and a 20 kHz high pass and a 4 kHz low pass filter was used.

Figure 2:
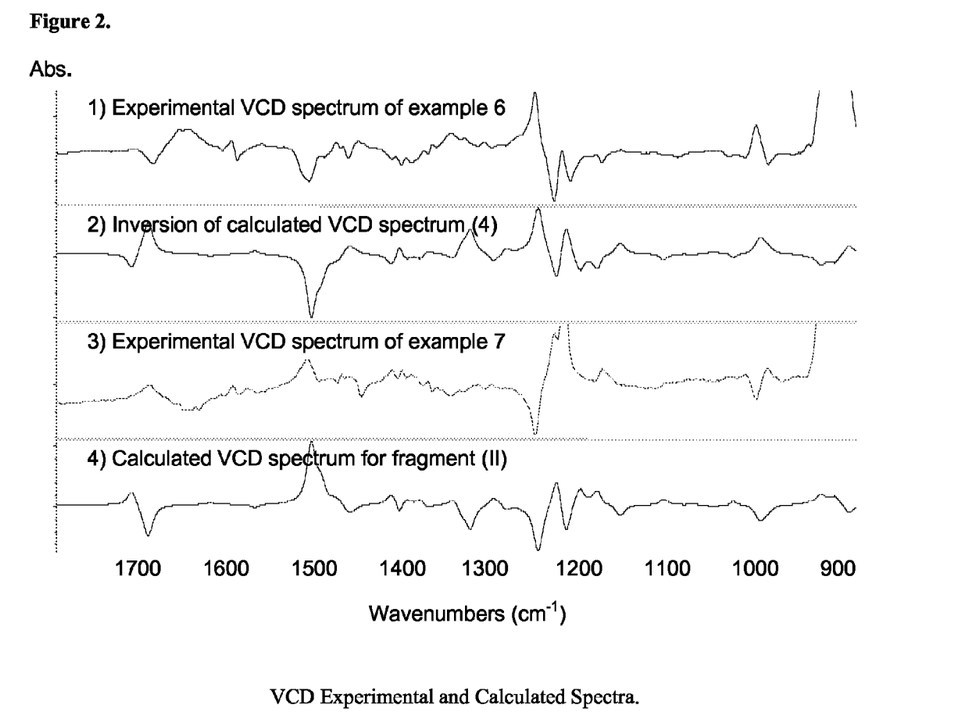
FIG. 2 shows VCD Spectra for compounds.

VCD Results:

FIG. 2 shows 4 spectra. Spectrum (1) is the experimentally collected spectrum of example 6. Spectrum (2) is a calculated estimation of the (R) enantiomer VCD spectrum which was obtained via inversion of the ab-initio calculated spectrum of fragment (II). Spectrum (3) corresponds to the experimental VCD spectrum of example 7. Spectrum (4) is the calculated spectrum for fragment (II), which is the (S)-enantiomer. Spectra 1 and 2 in FIG. 2 provide assignment of example 6 as the (R) enantiomer. The analogous comparison of Spectra 3 and 4 indicates example 7 to exist as the (S) enantiomer.

Biological Evaluation
Assay for Determining Biological Activity

The assay was designed to detect compounds that act on hTRPA1 by monitoring intracellular Ca$^{2+}$ levels in whole-cells. To this end, a dual addition step FLIPR (Fluorescence Imaging Plate Reader) assay for TRPA1 activity has been designed. Briefly, HEK293 cells expressing TRPA1 are grown in a 384 well microtitre plate and loaded with Fluo-4, a fluorescent probe that reports changes in intracellular calcium. TRPA1 channel activity is assayed by measuring a baseline signal in assay buffer, followed by application of an EC$_{80}$-concentration of the TRPA1-agonist zinc. The subsequent influx of calcium through TRPA1 channels is detected as a rise in cytoplasmic calcium, which in turn is reported as an increase in the Fluo-4 fluorescence. The activity of test compounds is assessed by adding compounds five minutes prior to the addition of zinc. TRPA1 blockers (antagonists) inhibit the calcium influx elicited by the zinc addition and hence no increase in Fluo-4 fluorescence occurs. TRPA1 openers (agonists) by themselves give rise to calcium influx and an increase in the Fluo-4 fluorescence detected immediately after compound addition.

In the assay expression of TRPA1 in the HEK293 cell line is under the control of an inducible promoter. Therefore, it is possible to establish the specificity of the TRPA1 signal by comparing the signal from the zinc stimulus on induced and non-induced cells.

TRPA1 is activated by a number of irritants that cause pain. Zinc is an essential biological trace element that excites nociceptive sensory neurons in mice in a TRPA1-dependent matter. Zinc activates TRPA1 through a unique mechanism that requires zinc influx through TRPA1 channels and subsequent activation via specific intracellular cysteine and histidine residues.

hTRPA1-HEK293-TREx cells were seeded in Poly-D-Lysine coated plate and allowed to grow a confluent monolayer in cell medium. Prior to the experiment the medium was discarded and cells loaded with fluo-4 NW (Molecular Probes) in assay buffer for 1 hour in room temperature. Compounds were added to the cell-plate and pre-incubated for 5 minutes in assay buffer without Ca$^{2+}$. 200 mM zinc$^{2+}$ in assay buffer with Ca$^{2+}$ was subsequently added to the cells and raw fluorescent counts measured using excitation LED-banks with wavelength 470-495 nm and emission filter with wavelength 515-575 nm. The typical assay conditions were: Test compounds: 30 μM to 0.001 μM, or zero in positive and negative controls; Assay buffer pH 7.4: HBSS with or without Ca$^{2+}$ and Mg$^{2+}$, 10 mM Hepes, 1 mM Glucose, 0.4% NaHCO$_3$, Agonist; 200 μM zinc chloride, Compounds to be tested were diluted in 100% DMSO and prior to the experiment further diluted 50 times in assay buffer.

In the assay 100% activity was defined as the peak fluorescence level caused by 200 μM zinc$^{2+}$ in absence of test compound. IC$_{50}$s represented the concentration of test compound required to inhibit this response with 50%.

Data from this assay for exemplified compounds is shown in the table below. The potency is expressed as IC$_{50}$ (concentration needed for 50% inhibition relative to the mean signal in calcium buffer) and the value indicated is an average of at least two individual experiments.

TABLE 1

| IC$_{50}$ values for the final compounds | |
|---|---|
| Example | Mean IC$_{50}$ (μM) |
| 5 (racemate) | 0.2 |
| 6 (R-enantiomer) | 0.06 |
| 7 (S-enantiomer) | 6.8 |

What is claimed is:

1. A compound N-(1-(4-cyanophenyl)-3,3-dimethyl-1-oxobutan-2-yl)-4-(6-methylpyridin-2-yl)piperazine-1-carboxamide of formula (I)

(I)

or a pharmaceutically acceptable salt thereof, enantiomer, or mixture thereof.

2. A compound according to claim 1 that is (R)—N-(1-(4-cyanophenyl)-3,3-dimethyl-1-oxobutan-2-yl)-4-(6-methylpyridin-2-yl)piperazine-1-carboxamide having the following formula:

or a pharmaceutically acceptable salt thereof.

3. A pharmaceutical composition comprising a compound according to claim 2 and a pharmaceutically acceptable carrier.

4. A method for the treatment of asthma, pertussis, nicotine addiction, acute pain disorders, or chronic pain disorders in a subject in need of such therapy, comprising administering to said subject a therapeutically effective amount of a compound according to claim 2.

5. A method for the treatment of pain in a subject in need of such therapy, comprising the step of administering to said subject a therapeutically effective amount of a compound according to claim 2.

6. The method of claim 4, wherein the acute pain disorder or chronic pain disorder is widespread pain, localized pain, nociceptive pain, inflammatory pain, central pain, central and peripheral neuropathic pain, central and peripheral neurogenic pain, central and peripheral neuralgia, chronic tendinitis, low back pain, postoperative pain, peripheral neuropathy, visceral pain, pelvic pain, allodynia, anesthesia dolorosa, causalgia, dysesthesia, fibromyalgia, hyperalgesia, hyperesthesia, hyperpathia, ischemic pain, sciatic pain, pain associated with cystitis, pain associated with multiple sclerosis, pain associated with arthritis, pain associated with osteoarthritis, pain associated with rheumatoid arthritis, or pain associated with cancer.

7. The method of claim 6, wherein the cystitis is interstitial cystitis.

* * * * *